US009782516B2

(12) United States Patent
Pacetti et al.

(10) Patent No.: US 9,782,516 B2
(45) Date of Patent: Oct. 10, 2017

(54) TISSUE ADHESIVE COATINGS FOR DRUG COATED BALLOON

(71) Applicant: ABBOTT CARDIOVASCULAR SYSTEMS INC., Santa Clara, CA (US)

(72) Inventors: Stephen D. Pacetti, San Jose, CA (US); John Stankus, Campbell, CA (US)

(73) Assignee: ABBOTT CARDIOVASCULAR SYSTEMS INC., Santa Clara, CA (US)

(*) Notice: Subject to any disclaimer, the term of this patent is extended or adjusted under 35 U.S.C. 154(b) by 0 days.

(21) Appl. No.: 13/842,445

(22) Filed: Mar. 15, 2013

(65) Prior Publication Data
US 2014/0277399 A1 Sep. 18, 2014

(51) Int. Cl.
A61F 2/00 (2006.01)
A61L 27/36 (2006.01)
A61L 31/16 (2006.01)

(52) U.S. Cl.
CPC ....... *A61L 27/3695* (2013.01); *A61L 27/3604* (2013.01); *A61L 31/16* (2013.01); *A61L 2400/06* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 5,102,402 A | 4/1992 | Dror et al. | |
| 5,324,261 A | 6/1994 | Amundson et al. | |
| 5,370,614 A | 12/1994 | Amundson et al. | |
| 6,129,705 A | 10/2000 | Grantz et al. | |
| 6,406,457 B1 | 6/2002 | Wang et al. | |
| 6,500,148 B1 | 12/2002 | Pinchuk et al. | |
| 6,991,617 B2 | 1/2006 | Hektner et al. | |
| 7,273,417 B1 | 9/2007 | Lundquist | |
| 8,049,061 B2 | 11/2011 | Ehrenreich et al. | |
| 8,226,603 B2 | 7/2012 | Von Oepen et al. | |
| 2003/0077317 A1* | 4/2003 | Santos ................ | A61K 9/1641 424/448 |
| 2005/0220853 A1* | 10/2005 | Dao .................... | A61K 9/7023 424/449 |
| 2007/0077435 A1* | 4/2007 | Schachter ............ | A61L 27/34 428/411.1 |
| 2007/0154466 A1* | 7/2007 | Weber ................. | A61K 31/727 424/94.4 |
| 2007/0215511 A1* | 9/2007 | Mehta et al. ................ | 206/531 |
| 2007/0244501 A1* | 10/2007 | Horn et al. ................... | 606/194 |
| 2009/0326638 A1* | 12/2009 | Atanasoska et al. ........ | 623/1.15 |
| 2010/0324645 A1* | 12/2010 | Stankus ............... | A61L 29/085 623/1.11 |
| 2011/0143017 A1 | 6/2011 | Stankus et al. | |
| 2011/0144578 A1* | 6/2011 | Pacetti ................. | A61L 29/085 604/96.01 |
| 2012/0015019 A1 | 1/2012 | Pacetti et al. | |

FOREIGN PATENT DOCUMENTS

| | | | |
|---|---|---|---|
| CN | 102781488 A | 11/2012 | |
| GB | 145629 A * | 9/1921 | ............... G01S 1/02 |

OTHER PUBLICATIONS

CRC (Critical Reviews in Biocompatibility) vol. 1, Issue 2, p. 112, Boca Raton, FL, CRC Press, 1985).
Carr, et al., "Effect of Homo Poly (L-Amino Acids) on Fibrin Assembly: Role of Charge and Molecular Weight", *Biochemistry*, 28(3):1384-1388 (1989).
Teltez, et al., "Luminal Fibrin as a Key Component in Mechanism of Action in Drug Coated Balloon Technologies", *New York-Presbyterian Hospital/Columbia University Medical Center*, Poster was advertised on Cardiovascular Research Foundation (TCT—Transcatheter Cardiovascular Therapeutics) in 2012,.
Giantsos, et al., The Use of an Endothelium-Targeted Cationic Copolymer to Enhance the Barrier Function of Lung Capillary Endothelial Monolayers, *Biomaterials*, 30(29):5885-5891 (2009).
Guccione, et al., "Reactions of Polylysine with Human Platelets in Plasma and in Suspension of Washed Platelets", *Thrombosis Haemost.* , 36(2):360-375 (1976).
Ong, et al., "Development of a Chitosan-Based Wound Dressing with Improved Hemostatic and Antimicrobial Properties", *Biomaterials*, 29(32):4323-4332 (2008).
Rosborough, "Von Willebrand Factor, Polyactions, and Planet Agglutination", *Thrombosis Res.*, 17(3-4):481-490 (1980).
Mohammad, et al., "Interactions of Poly (L-Lysine) with Human Platelets. Correlation of Binding with Induction of Platelet Aggregation", *Thrombosis Res.*, 15(5-6):781-791 (1979).
Unverdoben, Martin, "The Paclitaxel-Eluting PTCA-Balloon Catheter in Coronary Artery Disease PEPCAD I-SVD PEPCAD II-ISR", Clinical Research Institute, Center for Cardiovascular Diseases, 2005-2006, Rotenburg/Fulda, Germany.
Weyrich, et al., Mtor-Dependent Synthesis of Bcl-3 Controls the Retraction of Fibrin Clots by Activated Human Platelets , *Blood*, 109(5):1975-1983 (2007).
International Search Report and Written Opinion for PCT/US2013/032570, dated Jan. 2, 2014.

* cited by examiner

*Primary Examiner* — Susan Tran
(74) *Attorney, Agent, or Firm* — Baker Botts L.L.P.

(57) ABSTRACT

A therapeutic formulation is described for a drug delivery balloon comprising a therapeutic formulation which includes a therapeutic agent and an adhesion additive. The adhesion additive promotes adhesion of the therapeutic formulation a vessel wall of a subject. A system and a method of manufacturing a system including an expandable member having a working length with the therapeutic formulation disposed along at least a portion of the working length is also provided.

10 Claims, 5 Drawing Sheets

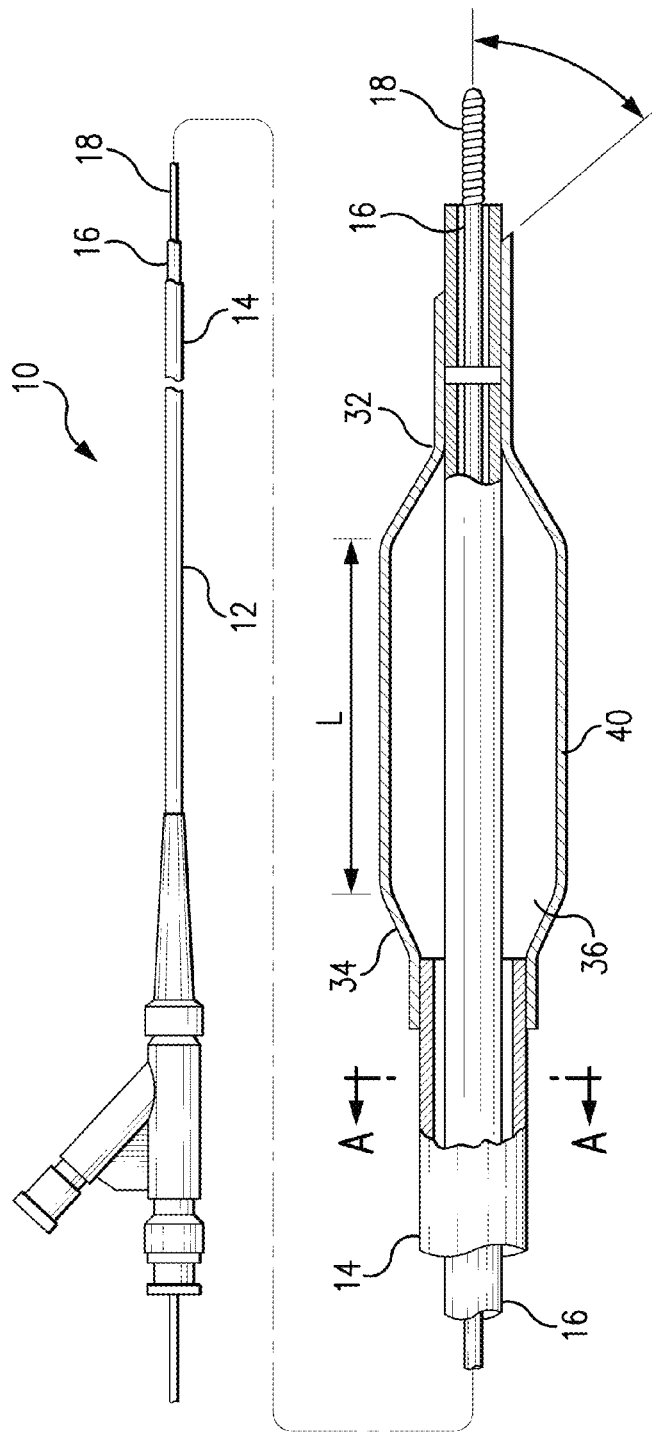
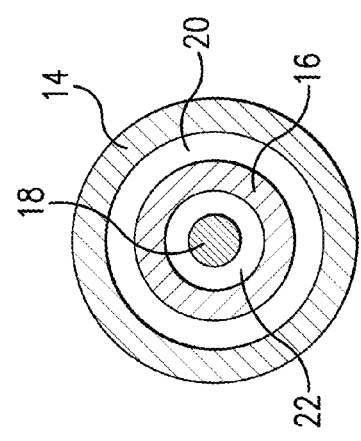
FIG. 1A
FIG. 1B

TISSUE ADHESIVE COATINGS FOR DRUG COATED BALLOON

FIELD OF THE INVENTION

The disclosed subject matter is related to the delivery of drugs from an insertable medical device. More particularly, the disclosed subject matter relates to a medical device including a balloon for delivery of a therapeutic agent, the balloon having a therapeutic formulation comprising a therapeutic agent and an adhesion additive to promote adhesion of the therapeutic formulation to the vessel wall.

BACKGROUND OF THE INVENTION

Atherosclerosis is a syndrome affecting arterial blood vessels. It leads to a chronic inflammatory response in the walls of arteries, which is in large part due to the accumulation of lipid, macrophages, foam cells and the formation of plaque in the arterial wall. Atherosclerosis is commonly referred to as hardening of the arteries although the pathophysiology of the disease manifests itself with several different types of lesions ranging from fibrotic to lipid laden to calcific. Angioplasty is a vascular interventional technique involving mechanically widening an obstructed blood vessel, typically caused by atherosclerosis.

During angioplasty, a catheter having a tightly folded balloon is inserted into the vasculature of the patient and is passed to the narrowed location of the blood vessel at which point the balloon is inflated to a fixed size using an inflation fluid, typically a solution of angiographic contrast media. Percutaneous coronary intervention (PCI), commonly known as coronary angioplasty, is a therapeutic procedure to treat the stenotic coronary arteries of the heart, often found in coronary heart disease.

In contrast, peripheral angioplasty, commonly known as percutaneous transluminal angioplasty (PTA), refers to the use of mechanical widening of blood vessels other than the coronary arteries. PTA is most commonly used to treat narrowing of the arteries of the leg, especially, the iliac, external iliac, superficial femoral and popliteal arteries. PTA can also treat narrowing of veins and other blood vessels.

It was determined that following angioplasty, although a blood vessel would be successfully widened, sometimes the treated wall of the blood vessel experienced abrupt closure after balloon inflation or dilatation, due to acute recoil or spasm. Interventional cardiologists addressed this problem by stenting the blood vessel to prevent acute recoil and vasospasm. A stent is a device, typically a metal tube or scaffold, which was inserted into the blood vessel following angioplasty, in order to hold the blood vessel open.

While the advent of stents eliminated many of the complications of abrupt vessel closure after angioplasty procedures, within about six months of stenting, a re-narrowing of the blood vessel can form, which is a condition known as restenosis. Restenosis was discovered to be a response to the injury of the angioplasty procedure and is characterized by a growth of smooth muscle cells—analogous to a scar forming over an injury. As a solution, drug eluting stents were developed to address the reoccurrence of the narrowing of blood vessels. One example of a drug eluting stent is a metal stent that has been coated with a drug that is known to interfere with the process of restenosis. A potential drawback of certain drug eluting stents is known as late stent thrombosis, which is an event in which blood clots form inside the stent.

Drug coated balloons are believed to be a viable alternative to drug eluting stents in the treatment of atherosclerosis. In a study which evaluated restenosis, and the rate of major adverse cardiac events such as heart attack, bypass, repeat stenosis, or death in patients treated with drug coated balloons and drug eluting stents, the patients treated with drug coated balloons experienced only 3.7 percent restenosis and 4.8% MACE as compared to patients treated with drug eluting stents, in which restenosis was 20.8 percent and 22.0 percent MACE rate. (See, PEPCAD II study, Rotenburg, Germany).

Although drug coated balloons are a viable alternative and in some cases may have greater efficacy than drug eluting stents as suggested by the PEPCAD II study, drug coated balloons present challenges due to the very short period of contact between the drug coated balloon surface and the blood vessel wall. The drug delivery time period for a drug coated balloon differs from that of a controlled release drug eluting stent, which is typically weeks to months. In particular for the coronary arteries, the balloon may only be inflated for less than one minute, and is often inflated for only thirty seconds. Therefore, an efficacious, therapeutic amount of drug must be transferred to the vessel wall within a thirty-second to one-minute time period. For the peripheral vasculature, the allowable inflation times can be greater than one minute, but are still measured in minutes. Thus, there are challenges specific to drug delivery via a drug coated balloon because of the necessity of a short inflation time, and therefore time for drug or coating transfer—a challenge not presented by a drug eluting stent, which remains in the patient's vasculature once implanted.

Various embodiments of drug-coated balloons have been proposed to address these needs, including balloons with a therapeutic agent disposed directly on the balloon surface and balloons having various protective sheaths. However, not all embodiments result in an efficacious response in reducing restenosis after balloon and/or bare metal stent trauma.

Therefore, a need exists for a drug delivery balloon, and more particularly, a balloon coated with a therapeutic agent that provides for effective delivery of the therapeutic agent from the surface of the balloon.

SUMMARY OF INVENTION

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

In accordance with an aspect of the disclosed subject matter, a system for delivering a therapeutic agent to a vessel wall of a subject is provided. The system includes an expandable member having a distal end, a proximal end, and a working length therebetween, and a therapeutic formulation. The therapeutic formulation is disposed on at least a portion of the working length of the expandable member. The therapeutic formulation comprises a therapeutic agent and an adhesion additive to promote adhesion of the therapeutic formulation to the vessel wall.

The adhesion additive as disclosed herein can include a polycationic polymer, a polyanionic polymer, a hemostat, or combinations thereof.

In accordance with one aspect of the disclosed subject matter, the adhesion additive adheres the therapeutic formulation to the endothelial tissue of the vessel wall after delivery from the expandable member, thereby promoting uptake of the therapeutic agent into the vessel wall. Suitable adhesion additives of this aspect include polycationic polymers and polyanionic polymers.

Further to the above, suitable polycationic polymers can include, for example, polyethyeneimine, polyallylamine, chitosan, poly-N-acetylglucosamine, poly(L-lysine), poly(D-lysine), poly(L-arginine), poly(D-arginine), poly(L-histidine), poly(D-histidine), and gelatin, or combinations thereof.

Alternatively, suitable polyanionic polymers include, without limitation, carboxymethyl cellulose, sodium carboxymethyl cellulose, carboxymethyl cellulose-cysteine, poly(acrylic acid). poly(methacrylic acid), poly(L-aspartic acid), poly(D-aspartic acid), poly(L-aspartic acid) sodium salt, poly(L-glutamic acid), poly(D-glutamic acid), poly(L-glutamic acid) sodium salt, or combinations thereof.

In accordance with another aspect of the disclosed subject matter, the adhesion additive promotes fibrin or thrombus formation on the vessel wall to promote adhesion of the therapeutic formulation to the vessel wall and thus uptake of the therapeutic agent. Suitable adhesion additives of this aspect include polycationic polymers and hemostatic agents.

Further to the above, suitable polycationic polymers include, without limitation, polyethyeneimine, polyallylamine, chitosan, poly-N-acetylglucosamine, poly(L-lysine), poly(D-lysine), poly(L-arginine), poly(D-arginine), poly(L-histidine), poly(D-histidine), gelatin, collagen, urinary bladder matrix, small intestinal submucosa, a decellularized extra-cellular matrix based material, or combinations thereof.

Additionally, suitable hemostatic agents include, for example, inorganic hemostats, small molecule hemostats, and peptide hemostats. Suitable inorganic hemostats include, without limitation, particulate hydroxyapatite, calcium chloride ($CaCl_2$), zinc chloride ($ZnCl_2$), silver nitrate ($AgNO_3$), ferric sulphate ($Fe_2(SO_4)_3$), and aluminum trichloride ($AlCl_3$). Suitable small molecule hemostats include, for example, tranexamic acid and aminocaproic acid. Suitable peptide hemostats include, without limitation, aprotinin.

The therapeutic agent of the disclosed subject matter can be zotarolimus, sirolimus, rapamycin, everolimus, biolimus, myolimus, novolimus, temsirolimus, deforolimus, merilimus, sirolimus derivatives, tacrolimus, pimecrolimus, dexamethasone, dexamethsone acetate, estradiol, paclitaxel, protaxel, taxane, docetaxel, angiopeptin, angiotensin converting enzyme inhibitors, captopril, cilazapril, lisinopril, calcium channel blockers, nifedipine, amlodipine, cilnidipine, lercanidipine, benidipine, trifluperazine, diltiazem, verapamil, fibroblast growth factor antagonists, fish oil, omega 3-fatty acid, histamine antagonists, lovastatin, topoisomerase inhibitors, etoposide, topotecan, antiestrogens, tamoxifen, derivatives and analogues thereof, or combinations thereof.

As embodied herein, the therapeutic agent is a cytostatic agent. Suitable cytostatic agents include zotarolimus, sirolimus, rapamycin, everolimus, biolimus, myolimus, novolimus, temsirolimus, deforolimus, merilimus, sirolimus derivatives, tacrolimus, pimecrolimus, derivatives and analogues thereof, and combinations thereof.

The therapeutic formation of the disclosed subject matter can further include at least one compound selected from the group consisting of surfactants, emulsifiers, solvents, plasticizers, and combinations thereof. For example, the plasticizer can be dimethysulfoxide (DMSO), polyethylene glycol (molecular weight <40K), propylene glycol, glycerol, N-Methyl-2-pyrrolidone (NMP), dimethylacetamide (DMAC), benzyl alcohol, fatty alcohols, benzyl benzoate, phenoxyethanol, and combinations thereof. For example, solvent can be acetone, 2-butanone, cyclopentanone, cyclohexanone, diethyl ether, dipropyl ether, diisopropyl ether, methyl acetate, ethyl acetate, propyl acetate, isopropyl acetate, butyl acetate, methanol, ethanol, n-propanol, isopropanol, n-butanol, isobutanol, sec-butanol, tertiary-butanol, toluene, xylene, pentane, hexane, cyclohexane, heptane, dimethylformamide (DMF), dimethylacetamide (DMAC), and combinations thereof.

In certain embodiments, the therapeutic formulation of the disclosed subject matter can further include a non-ionic polymer. For example, the non-ionic polymer can be polyvinylpyrrolidone (PVP), silk-elastin like polymer, poly(vinyl alcohol), poly(ethylene glycol) (PEG), pluronics (PEO-PPO-PEO), poly(vinyl acetate), poly(ethylene oxide) (PEO), PVP-vinyl acetate (copovidone), polysorbate 80 (TWEEN 80), and polysorbate 20 (TWEEN 20), hydroxyl alkyl celluloses, or combinations thereof. The adhesion additive promotes tissue adhesion of the non-ionic polymer to the vessel wall of the subject. Particular embodiments and formulations are set forth in further detail herein.

In one embodiment, the system of the disclosed subject matter further comprises a prosthesis mounted on the expandable member. The prosthesis can be a stent. In one embodiment, the expandable member is an angioplasty balloon.

Further in accordance with another aspect of the disclosed subject matter, a method for manufacturing a system for delivering a therapeutic agent to a vessel wall of a subject is provided. The method comprises providing a system comprising an expandable member having a distal end, a proximal end, and a working length therebetween; and disposing a therapeutic formulation to at least a portion of the working length of the expandable member. The formulation comprises a therapeutic agent and a polycationic polymer; wherein the polycationic polymer promotes fibrin formation that increases the residence time and transfer of the therapeutic agent into the vessel wall.

Further in accordance with another aspect of the disclosed subject matter, a method for manufacturing a system for delivering a therapeutic agent to a vessel wall of a subject is provided. The method comprises providing a system comprising an expandable member having a distal end, a proximal end, and a working length therebetween; and disposing a therapeutic formulation to at least a portion of the working length of the expandable member. The formulation comprises a therapeutic agent and an adhesion additive, wherein the adhesion additive promotes adhesion of the therapeutic formulation to the vessel wall.

The adhesion additive can be include a polycationic polymer, a polyanionic polymer, a hemostat, or combinations thereof.

Further in accordance with the disclosed subject matter, a method of treating a subject is provided. The method comprises providing any of the systems disclosed herein to a subject in need thereof.

It is to be understood that both the foregoing description and the following detailed description are exemplary and are intended to provide further explanation of the disclosed subject matter claimed.

The accompanying drawings, which are incorporated and constitute part of this specification, are included to illustrate and provide a further understanding of the systems of the disclosed subject matter. Together with the description, the drawings serve to explain the principles of the disclosed subject matter. The exemplified embodiments of the disclosed subject matter are not intended to limit the scope of the claims.

BRIEF DESCRIPTION OF DRAWINGS

The disclosed subject matter will now be described in conjunction with the accompanying drawings in which:

FIG. 1A is a schematic view of one representative balloon catheter in accordance with the disclosed subject matter; and FIG. 1B is a cross-sectional view taken along lines A-A in FIG. 1A in accordance with certain embodiments of the disclosed subject matter.

DETAILED DESCRIPTION

Figure 2:
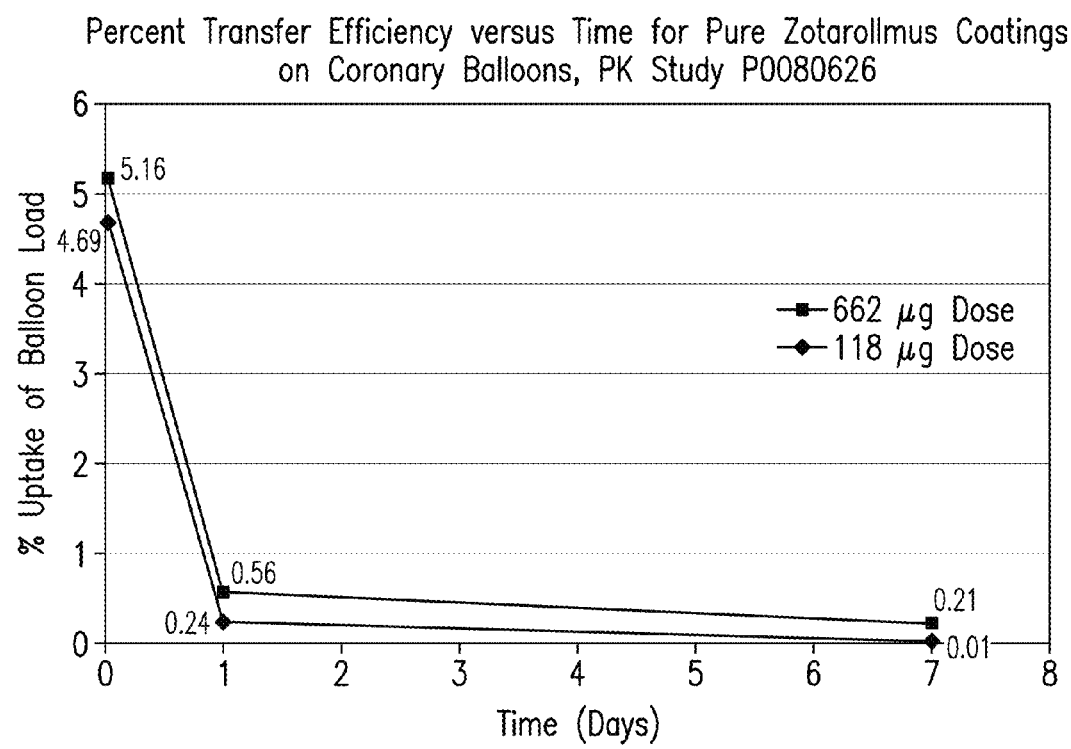
FIG. 2 is a graph illustrating percent transfer efficiency as a function of time for pure zotarolimus coatings on a zotarolimus coated balloon.

In accordance with an aspect of the disclosed subject matter, a system for delivering a therapeutic agent to a vessel wall of a subject is provided. The system includes an expandable member having a distal end, a proximal end, and a working length therebetween, and a therapeutic formulation. The therapeutic formulation is disposed on at least a portion of the working length of the expandable member. The therapeutic formulation comprises a therapeutic agent and an adhesion additive to promote adhesion of the therapeutic formulation to the vessel wall.

Reference will now be made in detail to the various aspects of the disclosed subject matter. The method of the disclosed subject matter will be described in conjunction with the detailed description of the system, the figures and examples provided herein.

Unless otherwise defined, all technical and scientific terms used herein have the same meanings as commonly understood by one of ordinary skill in the art to which the disclosed subject matter belongs. Although methods and materials similar or equivalent to those described herein can be used in its practice, suitable methods and materials are described below.

It is to be noted that the term "a" entity or "an" entity refers to one or more of that entity. As such, the terms "a", "an", "one or more", and "at least one" can be used interchangeably herein. The terms "comprising," "including," and "having" can also be used interchangeably. In addition, the terms "amount" and "level" are also interchangeable and can be used to describe a concentration or a specific quantity. Furthermore, the term "selected from the group consisting of" refers to one or more members of the group in the list that follows, including mixtures (i.e. combinations) of two or more members.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to +/−20%, or up to +/−10%, or up to +/−5%, or up to +/−1% of a given value. Alternatively, particularly with respect to biological systems or processes, the term can mean within an order of magnitude, or alternatively within 5-fold, or within 2-fold, of a value. With reference to pharmaceutical compositions, the term "about" refers to a range that is acceptable for quality control standards of a product approved by regulatory authorities.

The systems and methods presented can be used for delivery of a therapeutic agent to a vessel wall of a subject. The methods and systems presented herein can also be used for manufacture and assembly of medical devices such as a drug coated balloon catheter. While the disclosed subject matter references application of a therapeutic agent, it is to be understood that a variety of coatings including polymeric, therapeutic, or matrix coatings, can be applied to various surfaces of medical devices, as so desired.

Referring to FIG. 1, for purposes of illustration and not limitation, an exemplary embodiment of balloon catheter device in accordance with the disclosed subject matter is shown schematically in FIGS. 1A and 1B. As depicted in FIGS. 1A and 1B, the balloon catheter device 10 generally includes an elongated catheter shaft 12 having a proximal end and having a distal end and an expandable member or balloon 30 located proximate to the distal end of the catheter shaft. The expandable balloon has an outer surface and an inner surface disposed at the distal end portion of the catheter shaft. In accordance with the disclosed subject matter, a therapeutic formulation 40 is applied to at least a portion of the working length of the balloon catheter, the therapeutic formulation including a therapeutic agent and an adhesion additive, wherein the adhesion additive promotes adhesion of the therapeutic formulation to the vessel wall. In accordance with one aspect of the disclosed subject matter, as illustrated by way of example and not limitation in FIG. 1A, the therapeutic formulation is applied to at least a portion of the working length of the outer surface of the balloon catheter.

For purpose of illustration and not limitation, an elongated catheter shaft 12 having a coaxial arrangement is shown comprising an outer tubular member 14 and an inner tubular member 16. The outer tubular member 14 defines an inflation lumen 20 disposed between the proximal end portion and the distal end portion of the catheter shaft 12. For example, and as illustrated in FIG. 1B, the coaxial relationship between the inner tubular member 16 and the outer tubular member 14 defines an annular inflation lumen 20. The expandable member 30 is in fluid communication with the inflation lumen 20. The inflation lumen therebetween can supply fluid under pressure to the expandable member 30, and establish negative pressure to draw fluid from the expandable member 30. The expandable member 30 can thus be inflated and deflated. The elongated catheter is sized and configured for delivery through a tortuous anatomy, and can further include a guidewire lumen 22 that permits it to be delivered over a guidewire 18. As illustrated in FIG. 1B, the inner tubular member 16 defines the guidewire lumen 22 for the guidewire 18. Although FIGS. 1A and 1B illustrate the guidewire lumen as having an over-the-wire (OTW) construction, the guidewire lumen can be configured as a rapid-exchange (RX) construction, as is well known in the art. Similarly, the shaft can be provided as a multilumen member, or composition of two or more tubular members, as is known in the art.

As further depicted in FIG. 1A, the expandable member or balloon 30 has a distal end 32, a proximal end 34 and a working length therebetween. The expandable member embodied herein has a an interior chamber 36 in fluid communication with the inflatable lumen 20 of the elongated shart 12. Any of a number of suitable expandable member constructions and shapes can be used, as described further below. Further in accordance with the disclosed subject matter, a therapeutic formulation 40 comprising a therapeutic agent and an adhesion additive is disposed along at least a portion of the working length of the expandable member 30.

Adhesion Additives

In accordance with the disclosed subject matter, a system is provided for delivery of a therapeutic agent to a vessel wall of a subject, the system including an expandable member having a distal end, a proximal end, and a working length therebetween, and a therapeutic formulation disposed on at least a portion of the working length of the expandable member. The therapeutic formulation includes a therapeutic agent and an adhesion additive. The adhesion additive promotes adhesion of the therapeutic formulation to the vessel wall by adhering the therapeutic formulation to the vessel wall, and by additionally or alternatively promoting fibrin or thrombus formation on the vessel wall of a subject. Vessel wall transfer, retention and uptake are thereby increased by the adhesion additive The adhesion additive can be a polycationic polymer, an inorganic, small molecule or peptide hemostatic agent, a polyanionic polymer, or a combination thereof.

As used in accordance with the disclosed subject matter, an "adhesion additive" refers generally to a compound which promotes adhesion of the therapeutic formulation to the vessel wall and/or promotes and/or prolongs retention of the therapeutic formulation on the vessel wall after balloon inflation in the vessel. In certain embodiments, the adhesion additive will include at least one of a polyionic polymer or a hemostatic agent.

As used in accordance with the disclosed subject matter, a "polyionic polymer" refers to a polymer containing a number of different ions, e.g., sodium, potassium, chloride, bicarbonate. The polyionic polymer can be positively charged, which is referred to as "polycationic polymer," or the polyionic polymer can be negatively charged, which is referred to as "polyanionic polymer."

The polyionic polymer embodied herein, when used with a selected therapeutic agent, can promote adhesion of the therapeutic formulation by to the vessel wall by adhering the therapeutic formulation to the vessel wall. In comparison to non-ionic polymers, such as poly(ethylene glycol) (PEG), poly(vinyl pyrrolidone) (PVP), and hydroxy alkyl celluloses, which exhibit relatively low tissue adhesion, polyionic polymers exhibit much stronger adhesion to biological surfaces mediated by electrostatic interaction, hydration (or dehydration), hydrogen bonding and chain entanglement. In accordance with the disclosed subject matter, the polyionic polymers adhere the therapeutic formulation to the vessel wall to increase retention of a therapeutic agent on the vessel wall after delivery from an expandable member to the vessel wall. Thus, with a therapeutic formulation including a polyionic polymer on the expandable member, a greater amount of the therapeutic formulation adheres to the vessel wall upon inflation of the expandable member.

In certain embodiments of the disclosed subject matter, the polyionic polymer is a polyanionic polymer. Polyanionic polymers provide a tissue adhesive effect to increase retention of the therapeutic agent on the vessel wall after delivery from the expandable member to the vessel wall. In contrast to polycationic polymers, which employ a net positive charge to interact with the negatively charged surface of the endothelium, polyanionic polymers exhibit mucoadhesion whereby the multiple anionic charges present on the polymer, usually from carboxylate groups, bind via hydrogen bonding to the mucin or glycocalyx outer layer of biological surfaces. Suitable polyanionic polymers include, without limitation, carboxymethyl cellulose, sodium carboxymethyl cellulose, carboxymethyl cellulose-cysteine, poly(acrylic acid), poly(methacrylic acid), poly(L-aspartic acid), poly(D-aspartic acid), poly(L-aspartic acid) sodium salt, poly(L-glutamic acid), poly(D-glutamic acid), and poly(L-glutamic acid) sodium salt.

Carboxymethyl cellulose is used in the approved products Nutropin Depot (Genentech) and Bicillin (Wyeth). Polyamino acids can have a favorable safety profile but are much more expensive to employ. Homopolymers of amino acids that are un-branched are generally regarded as non-immunogenic. Poly(aspartic acid) and poly(glutamic acid) polymers have the requisite polyionic structural properties to be tissue adhesive, and both are commercially available in a range of molecular weights. Additionally, poly(aspartic acid) and poly(glutamic acid) polymers, which can be metabolized, can be used at a molecular weight above the 40K Dalton renal clearance threshold.

In alternative embodiments of the disclosed subject matter, the adhesive agent comprises a polycationic polymer. Polycationic polymers promote adhesion of the therapeutic formulation in part via relatively strong electrostatic interactions with the endothelial glycocalyx of the vessel surface, which is negatively charged (see Giantsos K M, et al. Biomaterials 30 (2009) 5885-5891). Suitable polycationic polymers which exhibit strong interactions with the endothelial surface include, without limitation, polyethyleneimine, polyallylamine, chitosan, poly-N-acetylglucosamine, poly(L-lysine), poly(D-lysine), poly(L-arginine), poly(D-arginine), poly(L-histidine), poly(D-histidine), and gelatin.

In further embodiments employing a polycationic polymer, the adhesive agent can be combined with dopamine to augment its tissue-adhesive properties. The dihydroxyphenol or catechol moiety found in dopamine provide adhesion to surfaces by hydrogen bonding and coordination mechanisms. Such moieties are ubiquitous in mussel and marine mollusk adhesive proteins.

Additionally or alternatively, the adhesion additive can promote adhesion of the therapeutic formulation to the vessel wall by the promotion of fibrin and thrombus formation. For example, and in accordance with certain embodiments of the disclosed subject matter, the polycationic polymer can provide such thrombus- and fibrin-promoting effect. For purpose of understanding and not limitation, platelets are negatively charged (see Ong S Y, et al. Biomaterials 29 (2008) 4323-4332. CRC Critical Reviews in Biocompatibility Vol 1, Issue 2, p. 112, Boca Raton, Fla., CRC Press, 1985). A wide variety of polycationic materials induce platelet agglutination by binding to the negatively charged platelet surface. Rosborough T K, Thrombosis Res, 1980, 17, 481. Positively charged poly(L-lysine), for example, enhances the association of fibrin protofibrils and increases the fibrin polymerization rate (see Carr M E, et al. Biochemistry 1989, 28, 1384-1388) and also induces platelet aggregation. Guccione M A, et al. Thrombo Haemostatsis, 1976, 36, 360. Mohammad S F, et al. Thrombosis Res, 1979, 15, 781-791. Platelets also have a net negative zeta potential, and accordingly are capable of aggregation in response to electrostatic forces. Polycationic polymers also encourage fibrin formation, so that the therapeutic formulation can adhere to the vessel wall via fibrin for a prolonged period of time.

The polycationic polymers possessing pro-thrombotic effect, e.g., fibrin forming tendency, include, for the purpose of illustration and without limitation, polyethyeneimine, polyallylamine, chitosan, poly-N-acetylglucosamine, poly(L-lysine), poly(D-lysine), poly(L-arginine), poly(D-arginine), gelatin, collagen, urinary bladder matrix (UBM), and combinations thereof. Polyethyeneimine and polyallylamine are both synthetic polycationic polymers. Low molecular weight grades of polyethyeneimine are available, which would allow passage through the kidney. Polyethyeneimine is alcohol soluble rendering formulation with a therapeutic agent, e.g., zotarolimus, straightforward. Chitosan is used in a variety of hemostatic agents for medical and military use. Chitosan has strong adhesive effect to tissue, wounds, and blood. Poly-N-acetylglucosamine is a polycationic polysaccharide. Poly-N-acetylglucosamine is the main component of the SyvekPatch hemostat approved by the Food and Drug Administration for use in the local management of bleeding wounds, such as vascular site, percutaneous catheters or tubes, and surgical debridement. In one embodiment, poly-N-acetyl glucosamine can be obtained from a marine microalgae. The polyamino acid poly(L-lysine) is available as the hydrochloride salt. Being a polyamino acid, poly(L-lysine) is reasonably biocompatible. Also, since it is a homopolymer polyamino acid, poly(L-lysine) has low immunogenicity. In one embodiment, the therapeutic formulation comprises zotarolimus and poly(L-lysine), wherein zotarolimus is in solution in an organic vehicle and poly(L-lysine) is in microsphere form. Gelatin is denatured collagen and has moderate cationic and pro-thrombotic properties. Collagen is pro-thrombotic to the extent that it stimulates a healing response. Typically, collagen accumulates a monolayer of activated platelets. Urinary bladder matrix (UBM), Small intestinal submucosa (SIS), other decellularized extra-cellular matrix (ECM) based materials are collagenous matrix that includes bioactive growth factors that readily accumulate activated platelets.

As an alternative, suitable hemostatic agents can be used as the adhesion additive to promote thrombus and fibrin formation for enhanced adhesion and retention of the therapeutic formulation. the adhesion additive is a hemostatic agent. By way of example and not limitation, hemostatic agents can promote platelet aggregation (i.e. thrombus formation) by promoting platelet and red blood cell aggregation. Alternatively, hemostatic agents can inhibit the activation of enzymes responsible for fibrin degradation. Furthermore, hemostatic agents can hasten and augment the natural fibrin and thrombus formation during the healing response after balloon inflation. Such augmentation of fibrin and/or thrombus growth likewise will result in increased adhesion of the therapeutic formulation and thus increase delivery of the therapeutic agent to the vessel wall. Suitable hemostatic agents include, without limitation, inorganic hemostatic agents, such as particulate hydroxyapatite, calcium chloride ($CaCl_2$), zinc chloride ($ZnCl_2$), silver nitrate ($AgNO_3$), ferric sulphate ($Fe_2(SO_4)_3$), and aluminum trichloride ($AlCl_3$), small molecule hemostats such as tranexamic acid and aminocaproic acid, and peptide hemostats such as aprotinin.

For purpose of explanation, and not limitation, of the disclosed subject matter, reference is now made to a comparative study between paclitaxel and zotarolimus. It has been observed that paclitaxel exhibits greater tissue retention than mTOR drugs delivered by balloon catheters. Table 1 shows a comparison of the transfer efficiency of different drugs with various therapeutic formulations from drug coated balloons.

TABLE 1

Characteristics and drug transfer efficiencies of drug coated balloons

| Formulation | Drug Dose ($\mu g/cm^2$) | Balloon Size (mm) | Implant location | Percent overstretch | Stent Present? | Inflation Time (second) | Time point | Percent transfer efficiency |
|---|---|---|---|---|---|---|---|---|
| Zotarolimus/Ultravist (1.95:1 w/w) | 270-320 | 3.0-3.5 × 17 | Coronary | 20% | Yes | 60 | 20 minutes | 6 |
| Pure everolimus or Everolimus/PVP/Glycerol | 730-1140 | 3 × 18 | Coronary | 20% | Yes | 30 | 24 hours | 0.4 |
| Pure Zotarolimus | 104 | 3 × 12 | Coronary | 20% | Yes | 30 | 30 minutes | 4.7 |
| Pure Zotarolimus | 576 | 3 × 12 | Coronary | 20% | Yes | 30 | 30 minutes | 5.2 |
| Zotarolimus/Ultravist (1.95:1 w/w) | 94 | 3 × 12 | Coronary | 20% | Yes | 30 | 30 minutes | 13.4 |
| Zotarolimus/PVP/Glycerol at a weight ratio of about 2:1:0.4 | 115 | 3 × 12 | Coronary | 20% | Yes | 30 | 30 minutes | 13.9 |
| Zotarolimus/PVP/Glycerol at a weight ratio of about 2:1:0.4 | 115 | 3 × 12 | Coronary | 20% | No | 30 | 30 minutes | 1.5 |
| Zotarolimus/PVP/Glycerol at a weight ratio of about 2:1:0.4 | 12 | 3 × 12 | Coronary | 20% | Yes | 30 | 30 minutes | 4.1 |
| Zotarolimus/PVP/Glycerol at a weight ratio of about 2:1:0.4 | 17 | 3 × 12 | Coronary | 20% | No | 30 | 30 minutes | 1.7 |
| Paclitaxel/Ultravist | 250 | 3.0-3.5 × 20 | Coronary | 20% | No | N/A | 40-60 minutes | 8.7 |

TABLE 1-continued

Characteristics and drug transfer efficiencies of drug coated balloons

| Formulation | Drug Dose ($\mu g/cm^2$) | Balloon Size (mm) | Implant location | Percent overstretch | Stent Present? | Inflation Time (second) | Time point | Percent transfer efficiency |
|---|---|---|---|---|---|---|---|---|
| Paclitaxel/Ultravist | 250 | 3.0-3.5 × 20 | Coronary | 20% | Stent then post-dilation with DCB | N/A | 40-60 minutes | 15.6 |
| Paclitaxel/Ultravist | 250 | 3.0-3.5 × 20 | Coronary | 20% | Yes | N/A | 40-60 minutes | 17.3 |

Figure 3:
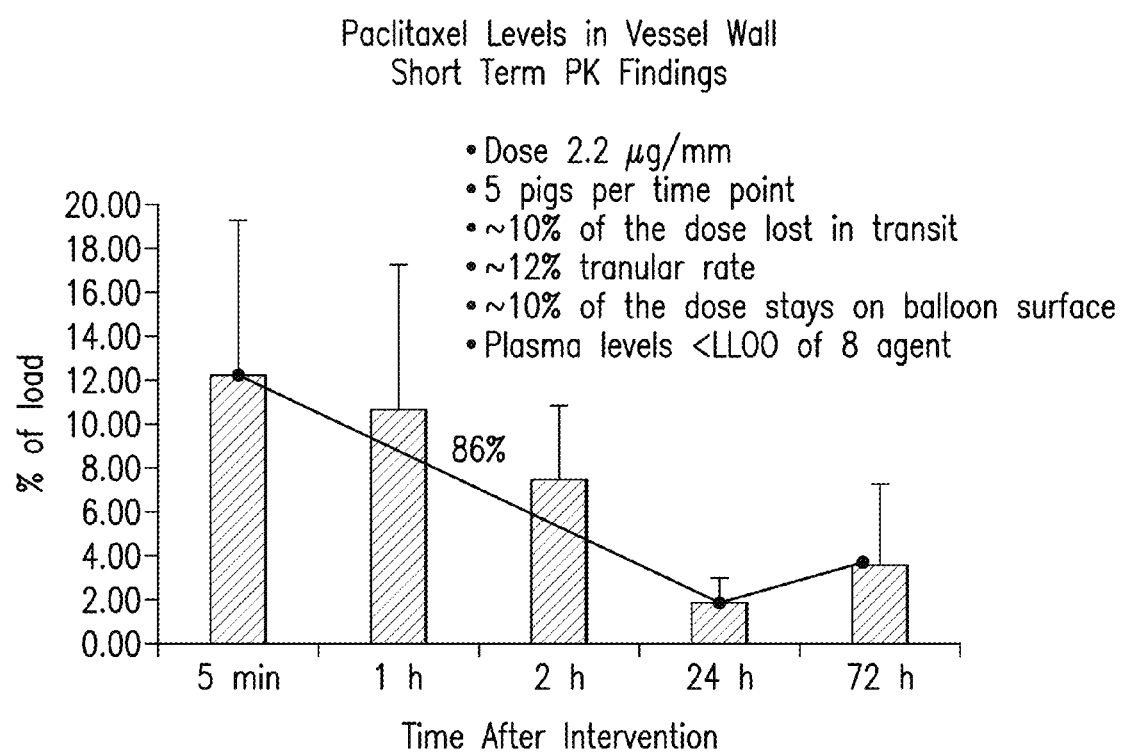
FIG. 3 is a graph illustrating percent tissue uptake of paclitaxel on a paclitaxel coated balloon.

As shown in Table 1, paclitaxel has a comparatively higher transfer efficiency than zotarolimus from a drug coated balloon. In addition, FIG. 2 shows the percent transfer efficiency for pure zotarolimus on a coronary balloon. With a stent on a coronary balloon, the percent of dose in the vessel from a pure zotarolimus coated balloon was measured at about 30 minutes, 1 day, and 7 days. As shown in FIG. 2, there was a rapid decrease in the percent drug in tissue as zotarelimus was cleared. Similar studies have been performed with a paclitaxel coated balloon in porcine coronary arteries as shown in FIG. 3. By comparison of FIGS. 2 and 3, the percent tissue uptake from a drug coated balloon for paclitaxel is greater than for pure zotarolimus. For example, at day 1 (24 hours), paclitaxel had about 2% of tissue uptake, while the higher dose zotarolimus (652 μg dose) had about 0.56% of tissue uptake.

Figure 4:
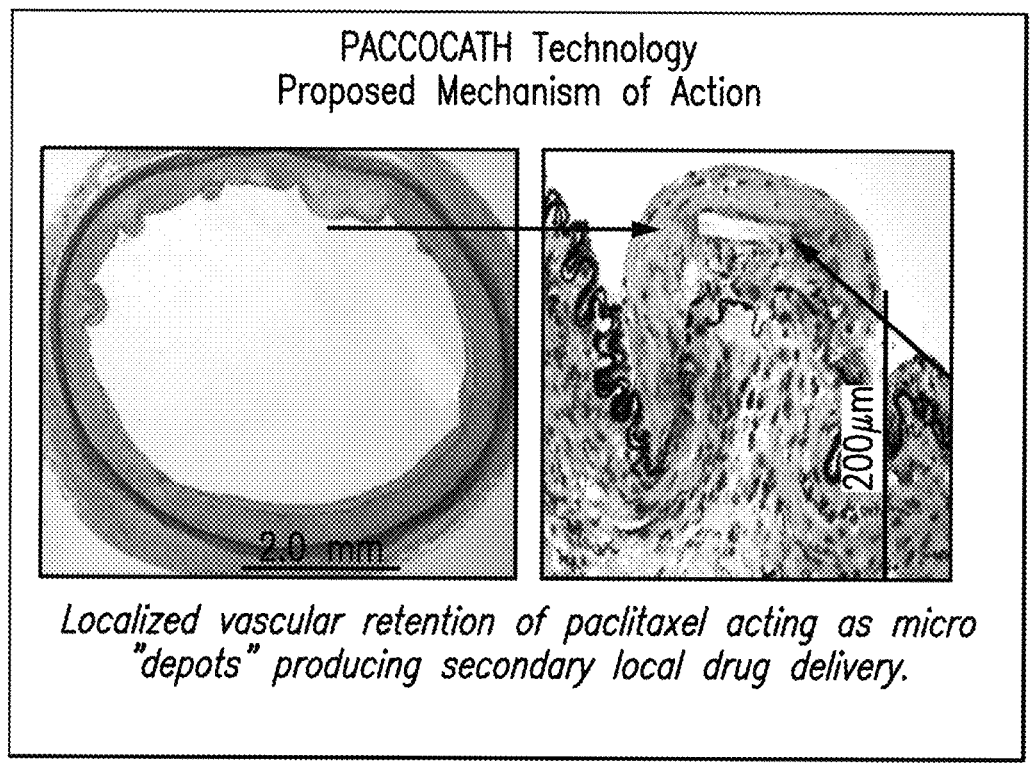
FIG. 4 is a graph illustrating retention of paclitaxel on a vessel wall by Paccocath technology.
Figure 5:
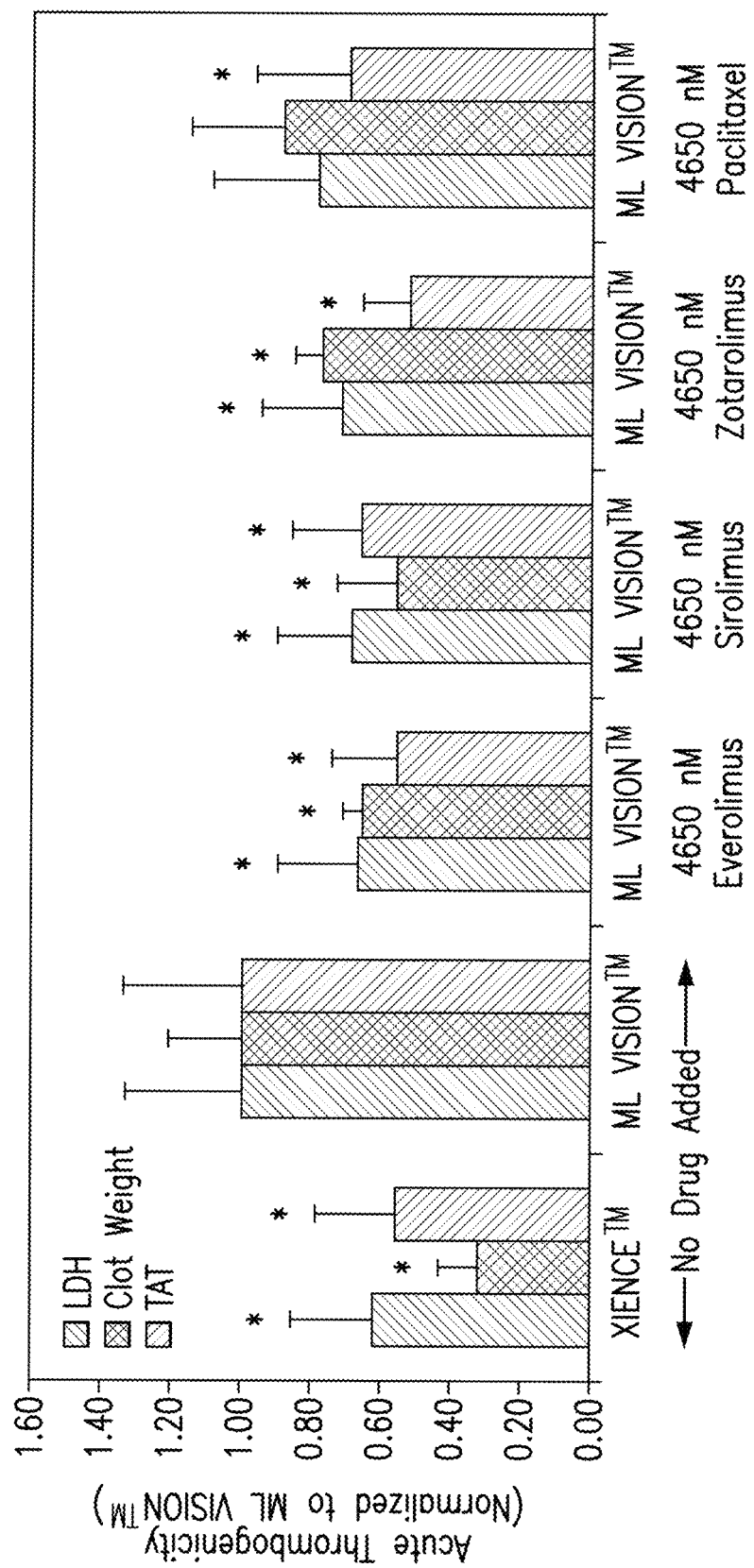
FIG. 5 is a graph illustrating acute thrombogenicity of drugs on drug coated stents.

Studies have been conducted to explain the high drug transfer efficiency or high tissue uptake exhibited by paclitaxel. It has been found that paclitaxel released from a paclitaxel coated balloon had a long residence or retention time on a vessel wall. FIG. 4 illustrates the mechanism of retention of paclitaxel on a vessel wall studied by Paccocath technology. PACCOCATH technology is the B. Braun technology using a mixture of the low-osmolar contrast agent Iopromide and paclitaxel. Iopromide is a low molecular weight, water soluble non-ionic contrast agent. The matrix is fragmented upon balloon inflation and dispersed; Iopromide dissolves and the lipophilic Paclitaxel adheres to the local endothelial surface. In the right panel of FIG. 4, the highlighted material enclosed in fibrin is purported to be paclitaxel. Iopromide is completely water soluble, and therefore has no lifetime on the vessel wall. It therefore has been posited that paclitaxel is attached to the vessel wall by fibrin formed during the thrombotic cascade of the healing process when a vessel is injured. By contrast, there has been no apparent histology evidence of pure zotarolimus coating fragments adhering to a vessel wall in a similar manner. One theory to explain the difference in retention time on a vessel wall is that zotarolimus has a lower inherent thrombogenicity than paclitaxel. FIG. 5 shows the measurement of acute thrombogenicity of stents in whole blood via the Chandler Loop with various concentrations of zotarolimus, everolimus, sirolimus, and paclitaxel. As shown in FIG. 5, compared to zotarolimus, paclitaxel is more thrombogenic as measured by clot weight and lactate dehydrogenase (LDH) but not by thrombin-antithrombin (TAT). Additional studies directly confirm these observations.

Sirolimus has been demonstrated to inhibit the retraction of fibrin via platelets, which inhibits formation of a solid clot (see Weyrich A S, et al. Blood 2007; 109:1975-1983). Such a result is due to mammalian target of rapamycin (mTOR) inhibition, which is also inhibited by zotarolimus. Hence, and in view of the above, a therapeutic formulation including an adhesion additive to promote retention of cytostatic mTOR drugs at the vessel wall will result in improved tissue adhesion, and thus improved tissue uptake of the cytostatic mTOR drug and corresponding improvements in efficacy.

Therapeutic Agents

In accordance with the disclosed subject matter, and for purpose of illustration and not limitation, the therapeutic agent or drug can include any of a variety of suitable anti-proliferative, anti-inflammatory, anti-neoplastic, anti-platelet, anti-coagulant, anti-fibrin, anti-thrombotic, anti-mitotic, antibiotic, anti-allergic and antioxidant compounds. Thus, the therapeutic agent can be, again without limitation, a synthetic inorganic or organic compound, a protein, a peptide, a polysaccharides and other sugars, a lipid, DNA and RNA nucleic acid sequences, an antisense oligonucleotide, an antibody, a receptor ligands, an enzyme, an adhesion peptide, a blood clot agent including streptokinase and tissue plasminogen activator, an antigen, a hormone, a growth factor, a ribozyme, and a retroviral vector.

The term "anti-proliferative" as used herein means an agent used to inhibit cell growth, such as chemotherapeutic drugs. Some non-limiting examples of anti-proliferative drugs include taxanes, paclitaxel, docetaxel, and protaxel. Anti-proliferative agents can be anti-mitotic. The term "anti-mitotic" as used herein means an agent used to inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, including, for example, daunorubicin, daunomycin, and plicamycin. Other sub-classes of anti-mitotic agents include anti-mitotic alkylating agents, including, for example, tauromustine, bofumustine, and fotemustine, and anti-mitotic metabolites, including, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing. An example of an anti-mitotic agent includes, but is not limited to, paclitaxel. As used herein, paclitaxel includes the alkaloid itself and naturally occurring forms and derivatives thereof, as well as synthetic and semi-synthetic forms thereof.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, including, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpIIbIIIa or avb3, antibodies that block binding to gpIIaIIIb or avb3, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

As discussed above, at least one therapeutic agent can be an anti-inflammatory agent. Non-limiting examples of anti-inflammatory agents include prednisone, dexamethasone, dexamethasone acetate, hydrocortisone, estradiol, triamcinolone, mometasone, fluticasone, clobetasol, and non-steroidal anti-inflammatories, including, for example, acetaminophen, ibuprofen, naproxen, adalimumab and sulindac. The arachidonate metabolite prostacyclin or prostacyclin analogs is an example of a vasoactive antiproliferative. Other examples of these agents include those that block cytokine activity or inhibit binding of cytokines or chemokines to the cognate receptors to inhibit pro-inflammatory signals transduced by the cytokines or the chemokines. Representative examples of these agents include, but are not limited to, anti-IL1, anti-IL2, anti-IL3, anti-IL4, anti-IL8, anti-IL15, anti-IL18, anti-MCP1, anti-CCR2, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, including, for example, heparin, heparin sulfate, low molecular weight heparins, including, for example, the compound having the trademark Clivarin®, and synthetic oligosaccharides, including, for example, the compound having the trademark Arixtra®. Also included are direct thrombin inhibitors, including, for example, melagatran, ximelagatran, argatroban, inogatran, and peptidomimetics of binding site of the Phe-Pro-Arg fibrinogen substrate for thrombin. Another class of anti-thrombotic agents that can be delivered is factor VII/VIIa inhibitors, including, for example, anti-factor VII/VIIa antibodies, rNAPc2, and tissue factor pathway inhibitor (TFPI).

Thrombolytic agents, which can be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

Furthermore, the therapeutic agents include a cytostatic agent. The term "cytostatic" as used herein means an agent that mitigates cell proliferation, allows cell migration, and does not induce cell toxicity. These cytostatic agents include, for the purpose of illustration and without limitation, macrolide antibiotics, zotarolimus, sirolimus, rapamycin, everolimus, biolimus, myolimus, novolimus, temsirolimus, deforolimus, merilimus, sirolimus derivatives, tacrolimus, pimecrolimus, derivatives and analogues thereof, any macrolide immunosuppressive drugs, and combinations thereof. Other therapeutic agents include cytotoxic drugs, including, for example, apoptosis inducers, including TGF, and topoisomerase inhibitors, including, 10-hydroxycamptothecin, irinotecan, and doxorubicin.

In certain embodiments of the disclosed subject matter, the cytostatic agent can be provided wholly or in part in crystalline form. For illustration and not limitation, such crystalline cytostatic agents can comprise relatively larger, less soluble particles of the cytostatic agent that amorphous forms of the cytostatic agent. Such larger, less soluble particles of the cytostatic agent can in some embodiments further promote fibrin attachment to the cytostatic agent and thereby promote retention of the cytostatic agent at the tissue.

In certain embodiments, the therapeutic formulation of the disclosed subject matter comprises zotarolimus and poly(L-glutamic acid). In one embodiment, the formulation further comprises glycerol. The ratio of zotarolimus:poly(L-glutamic acid):glycerol is about 2:1:0.4 by weight. In one embodiment, the therapeutic formulation comprises paclitaxel and sodium carboxymethyl cellulose. The formulation can further comprise DMSO. The ratio of paclitaxel:sodium carboxymethyl cellulose:DMSO is about 1:1:0.2 by weight. In another embodiment, the therapeutic formulation comprises everolimus and poly(L-glutamic acid). In one embodiment, the poly(L-glutamic acid) is combined with dopamine in the form of poly(L-glutamic acid)-dopamine. The ratio of everolimus:poly(L-glutamic acid)-dopamine is about 2:1 by weight.

In further representative embodiments, the therapeutic formulation of the disclosed subject matter comprises zotarolimus and polyethyeneimine. The ratio of zotarolimus:polyethyeneimine is about 1:1 by weight. The therapeutic formulation can further comprise zotarolimus and poly(L-lysine). The ratio of zotarolimus:poly(L-lysine) is about 1:1 by weight.

Additional Optional Components of the Therapeutic Formulation

In accordance with the disclosed subject matter, the therapeutic formulation can further include at least one compound selected from the group consisting of surfactants, emulsifiers, solvents, plasticizers, and combinations thereof.

In certain embodiments, the therapeutic formulation further includes a plasticizer. Polyionic polymers are highly polar and soluble in water or highly polar solvents, such as dimethysulfoxide (DMSO), Dimethylacetamide (DMAC), and ethanol. Due to their high polarity and hydrogen bonding, polyionic polymers have Tgs above ambient temperature in the dry state. Consequently, a dry coating of polyionic polymers can be brittle and may have poor coating integrity. A solution to provide for good coating integrity when dry is to plasticize the therapeutic formulation with an appropriate plasticizer. Suitable plasticizers are low molecular weight, and water soluble species that are essentially non-volatile. The plasticizers include, for the purpose of illustration and without limitation, dimethysulfoxide (DMSO), polyethylene glycol (molecular weight <40K), propylene glycol, glycerol, N-Methyl-2-pyrrolidone (NMP), dimethylacetamide (DMAC), benzyl alcohol, fatty alcohols, benzyl benzoate, phenoxyethanol, and combinations thereof. In some embodiments, the plasticizer, such as DMSO, increases lipid fluidity, and thus, enhances drug penetration and permeability in the tissue.

In further embodiments, the therapeutic formulation further includes a solvent. The solvents include, for the purpose of illustration and without limitation, acetone, 2-butanone, cyclopentanone, cyclohexanone, diethyl ether, dipropyl ether, diisopropyl ether, methyl acetate, ethyl acetate, propyl acetate, isopropyl acetate, butyl acetate, methanol, ethanol, n-propanol, isopropanol, n-butanol, isobutanol, sec-butanol, tertiary-butanol, toluene, xylene, pentane, hexane, cyclohexane, heptane, dimethylformamide (DMF), dimethylacetamide (DMAC), and combinations thereof.

In accordance with the disclosed subject matter, the therapeutic formulation can further include a non-ionic polymer. The polyionic polymer increases tissue adhesion of the non-ionic polymer to a vessel wall of a subject. For example, PVP can be blended with a smaller portion of carboxymethyl cellulose or poly(aspartic acid) for enhanced tissue adhesion. Poly(acrylic acid) can be grafted with PEG chains to promote further interpenetration within a mucus gel. PEG can be functionalized with cysteine groups to increase tissue adhesion through disulfide bonding. The non-ionic polymers include, for the purpose of illustration and without limitation, PVP, silk-elastin like polymer, poly(vinyl alcohol), PEG, pluronics (PEO-PPO-PEO), poly(vinyl acetate), poly(ethylene oxide) (PEO), PVP-vinyl acetate (copovidone), polysorbate 80 (Tween 80), and polysorbate 20 (Tween 20), hydroxyl alkyl celluloses, and combinations thereof.

Additional System Components

A wide variety of balloon catheters and balloon constructs are known and suitable for use in accordance with the disclosed subject matter. For purpose of illustration and not limitation, the expandable member is fabricated from polymeric material such as compliant, non-compliant or semi-compliant polymeric material or polymeric blends (e.g., a mixture of polymers). In one embodiment, the polymeric material is compliant such as but not limited to a polyamide/polyether block copolymer (commonly referred to as PEBA or polyether-block-amide). In certain embodiments, the polyamide and polyether segments of the block copolymers can be linked through amide or ester linkages. The polyamide block can be selected from various aliphatic or aromatic polyamides known in the art. In some embodiments, the polyamide is aliphatic. Some non-limiting examples include nylon 12, nylon 11, nylon 9, nylon 6, nylon 6/12, nylon 6/11, nylon 6/9, and nylon 6/6. In some embodiments, the polyamide is nylon 12. The polyether block can be selected from various polyethers known in the art. Some non-limiting examples of polyether segments include poly(tetramethylene ether), tetramethylene ether, polyethylene glycol, polypropylene glycol, poly(pentamethylene ether) and poly(hexamethylene ether). Commercially available PEBA material can also be utilized such as for example, PEBAX® materials supplied by Arkema (France). Various techniques for forming a balloon from polyamide/polyether block copolymer is known in the art. One such example is disclosed in U.S. Pat. No. 6,406,457 to Wang, the disclosure of which is incorporated by reference.

In additional embodiments, the balloon material is formed from polyamides. In some embodiments, the polyamide has substantial tensile strength, be resistant to pin-holing even after folding and unfolding, and be generally scratch resistant, such as those disclosed in U.S. Pat. No. 6,500,148 to Pinchuk, the disclosure of which is incorporated herein by reference. Some non-limiting examples of polyamide materials suitable for the balloon include nylon 12, nylon 11, nylon 9, nylon 69 and nylon 66. In some embodiments, the polyamide is nylon 12. Other suitable materials for constructing non-compliant balloons are polyesters such as poly(ethylene terephthalate) (PET), Hytrel thermoplastic polyester, and polyethylene.

In additional embodiments, the balloon is formed of a polyurethane material, such as TECOTHANE® (Thermedics). TECOTHANE® is a thermoplastic, aromatic, polyether polyurethane synthesized from methylene disocyanate (MDI), polytetramethylene ether glycol (PTMEG) and 1,4 butanediol chain extender. TECOTHANE® grade 1065 D is suitable in certain embodiments, and has a Shore durometer of 65 D, an elongation at break of about 300%, and a high tensile strength at yield of about 10,000 psi. However, other suitable grades can be used, including TECOTHANE® 1075 D, having a Shore D hardness of 75. Other suitable compliant polymeric materials include ENGAGE® (DuPont Dow Elastomers (an ethylene alpha-olefin polymer) and EXACT® (Exxon Chemical), both of which are thermoplastic polymers. Other suitable compliant materials include, but are not limited to, elastomeric silicones, latexes, and urethanes.

The compliant material can be cross linked or uncrosslinked, depending upon the balloon material and characteristics required for a particular application. In certain embodiments, the polyurethane balloon materials are not crosslinked. However, other suitable materials, such as the polyolefinic polymers ENGAGE® and EXACT®, can be crosslinked. By crosslinking the balloon compliant material, the final inflated balloon size can be controlled. Conventional crosslinking techniques can be used including thermal treatment and E-beam exposure. After crosslinking, initial pressurization, inflation, and preshrinking, the balloon will thereafter expand in a controlled manner to a reproducible diameter in response to a given inflation pressure, and thereby avoid overexpanding the stent (if used in a stent delivery system) to an undesirably large diameter.

In one embodiment, the balloon is formed from a low tensile set polymer such as a silicone-polyurethane copolymer. In some embodiments, the silicone-polyurethane is an ether urethane and more specifically an aliphatic ether urethane such as PURSIL AL 575A and PURSIL AL10, (Polymer Technology Group), and ELAST-EON 3-70A, (Elastomedics), which are silicone polyether urethane copolymers, and more specifically, aliphatic ether urethane cosiloxanes. In an alternative embodiment, the low tensile set polymer is a diene polymer. A variety of suitable diene polymers can be used such as but not limited to an isoprene such as an AB and ABA poly(styrene-block-isoprene), a neoprene, an AB and ABA poly(styrene-block-butadiene) such as styrene butadiene styrene (SBS) and styrene butadiene rubber (SBR), and 1,4-polybutadiene. In certain embodiments, the diene polymer is an isoprene including isoprene copolymers and isoprene block copolymers such as poly(styrene-block-isoprene). A suitable isoprene is a styrene-isoprene-styrene block copolymer, such as Kraton 1161K available from Kraton, Inc. However, a variety of suitable isoprenes can be used including HT 200 available from Apex Medical, Kraton R 310 available from Kraton, and isoprene (i.e., 2-methyl-1,3-butadiene) available from Dupont Elastomers. Neoprene grades useful in the disclosed subject matter include HT 501 available from Apex Medical, and neoprene (i.e., polychloroprene) available from Dupont Elastomers, including Neoprene G, W, T and A types available from Dupont Elastomers.

In accordance with another aspect of the disclosed subject matter, the outer surface of the balloon is modified. In this regard, the balloon surface can include a textured surface, roughened surface, voids, spines, channels, dimples, pores, or microcapsules or a combination thereof, as will be described below.

In accordance with the disclosed subject matter, the balloon does not necessarily include a stent, e.g., is free of a stent. However, a stent can be mounted onto the coated balloon and can further promote uptake. The stent will not detrimentally affect coating integrity or drug delivery. The type of stent that can be used includes, but is not limited to, a bare metal stent, a balloon expandable stent, a self expanding stent, a drug eluting stent, a prohealing stent, and a self-expanding vulnerable plaque implant. The balloon can be coated independently of the stent or in conjunction with the stent coating process. The stent coating can contain the same or different therapeutic agents from the balloon catheter or expandable member. However, the particular coating on the balloon catheter or expandable member can have distinct release kinetics from the therapeutic coating on the stent.

In further embodiments of the disclosed subject matter, the balloon is formed of a porous elastomeric material having at least one void formed in the wall of the balloon surface. For example, the entire cross section of the balloon can contain a plurality of voids. Alternatively, the plurality of void can be distributed along select lengths of the balloon outer surface. For example and not limitation, the plurality of voids can be distributed only along the working section of the balloon. The voids define an open space within the outer surface of the balloon. In some embodiments, the therapeutic agent is dispersed within the space defined by the plurality of voids across the cross section of the balloon outer surface.

In operation, the therapeutic agent is released or is expelled from the pores upon inflation of the balloon. In this regard, the durometer of the polymeric material of the balloon surface and in particular the depression of the void is sufficiently flexible to allow for expulsion of the therapeutic agent and/or coating contained within the plurality of voids upon inflation of the balloon. The expelled coating with therapeutic agent is released into the vessel lumen or into the tissue surrounding and contacting the inflated balloon.

In additional embodiments, the balloon includes protrusions configured to contact or penetrate the arterial wall of a vessel upon inflation of the balloon. A therapeutic formulation is disposed on the protrusions and when inflated the therapeutic formulation and/or therapeutic agent coats or adheres to the tissue of the arterial wall. Alternatively, the balloon can include two concentric balloons in a nesting configuration. The therapeutic formulation is disposed between the two concentric balloons. Thus, the space between the two concentric balloons; one being an interior balloon and the other being an exterior balloon, acts as a reservoir. In this regard, the protrusions can include apertures for expulsion of the therapeutic formulation and/or therapeutic agent upon inflation of the interior and exterior concentric balloons. For example, as described in U.S. Pat. No. 6,991,617 to Hektner, the disclosure of which is incorporated herein by reference thereto. In another embodiment, the balloon can include longitudinal protrusions configured to form ridges on the balloon surface. As described in U.S. Pat. No. 7,273,417 to Wang, the entire disclosure of which is incorporated herein by reference, the ridges can be formed of filaments spaced equidistantly apart around the circumference of the balloon. However, a larger or smaller number of ridges can alternatively be used. The longitudinal ridges can be fully or partially enveloped by the polymeric material of the balloon.

In still further embodiments of the disclosed subject matter, the balloon can include microcapsules on its outer surface. In this regard, the microcapsules are configured to encompass the therapeutic formulation and/or therapeutic agent. Upon inflation of the balloon the microcapsules located on the surface of the balloon contact the tissue of the arterial wall. Alternatively, the microcapsules can be formed in the wall of the balloon surface. The therapeutic formulation and/or therapeutic agent can be released from the microcapsules by fracturing of the microcapsules and/or diffusion from the microcapsule into the arterial wall. The microcapsules can be fabricated in accordance with the methods disclosed in U.S. Pat. No. 5,1023,402 to Dror or U.S. Pat. No. 6,129,705 to Grantz and the patents referenced therein, each of which is incorporated herein by reference in its entirety.

In accordance with another aspect of the disclosed subject matter, if desired, a protective sheath can be utilized to protect the therapeutic formulation from being rubbed off of the balloon during the movement of the coated balloon through the body lumen. In some embodiments, the sheath is made from an elastic and resilient material which conforms to the shape of the balloon and in particular is capable of expanding upon inflation of the balloon. The sheath can include apertures along a length thereof. In operation, the inflation of the balloon causes the apertures of the sheath to widen for release of the therapeutic formulation and/or therapeutic agent to the tissue of the arterial wall. In some embodiments, the sheath has a thickness less than 10 mils. However, other thicknesses are possible.

In additional embodiments, the sheath has at least one longitudinal line of weakness allowing the sheath to rupture upon inflation of the balloon and the release of the therapeutic formulation and/or therapeutic agent onto the tissue of the arterial wall of the vessel. In some embodiments, the sheath is formed from polymeric material known to be suitable for use in balloon catheters. The sheath material can be an elastomeric material which will also spring back when it splits to expose more of the body lumen to the coating. The line of weakness could be provided by various techniques known in the art. However, one non-limiting examples include perforating the sheath material. In operation, the sheath is placed over the coated balloon while in the deflated state. When the coated balloon is inflated, the sheath is expanded to the extent that it exceeds its elastic limit at the line of weakness and bursts to expose and therefore release the therapeutic formulation and/or therapeutic agent to the tissue of the arterial wall or vessel lumen. For example, see U.S. Pat. No. 5,370,614 to Amundson, the entire disclosure of which is incorporated by reference.

In accordance with additional embodiments, an outer fibrous coating can be electrospun or stretched onto the medical device or balloon catheter to prevent drug loss during delivery. During balloon inflation, the therapeutic formulation or coating is stretched and allows for coating solubilization and release. The fiber diameters and material properties can be fine tuned for optimal pore size and to release the particles containing the therapeutic agent. Fibrous coatings on expandable members are described in U.S. patent application Ser. No. 12/237,998 to R. von Oepen and U.S. patent application Ser. No. 12/238,026 to K. Ehrenreich, the disclosures of which are incorporated by reference in their entirety.

EXAMPLES

The present application is further described by means of the examples, presented below. The use of such examples is illustrative only and in no way limits the scope and meaning of the disclosed subject matter or of any exemplified term.

Example 1

A therapeutic formulation was made comprising zotarolimus, poly(L-glutamic acid) (sodium salt, MW=50-70K), and glycerol at a weight ratio of about 2:1:0.4 at about 3% total solids in a solvent system of ethanol/water. VISION balloons, 3×12 mm, were plasma treated and this therapeutic formulation was applied by spray to achieve a drug loading of about 500 μg zotarolimus on the balloon. After application, the therapeutic formulation was dried in a forced air convection oven for about 60 minutes at about 50° C.

Example 2

A therapeutic formulation was made comprising paclitaxel, sodium carboxymethyl cellulose (sodium salt, low viscosity grade, MW=90K), and DMSO at a weight ratio of about 1:1:0.2 at about 3% total solids in a solvent system of DMF/ethanol/water. VISION balloons, 3×12 mm, were plasma treated and this therapeutic formulation was applied by direct syringe application to achieve a drug loading of about 340 μg paclitaxel on the balloon. After application, the therapeutic formulation was dried in a forced air convection oven for about 60 minutes at about 50° C.

Example 3

The protonated form of poly(L-glutamic acid) was made by adding poly(L-glutamic acid), sodium salt to an aqueous solution titrated to pH 2-4 with HCl, and extracting the neutral poly(L-glutamic acid) (PGA) into chloroform. After isolation, the neutral PGA was combined with dopamine to make the organic soluble PGA-dopamine salt. A therapeutic formulation was made comprising everolimus and PGA-dopamine at a weight ratio of about 2:1 at about 3% total solids in a solvent system of acetone/ethanol. VISION balloons, 3×12 mm, were plasma treated and this therapeutic formulation was applied by direct syringe application to achieve a drug loading of about 100 μg of everolimus on the balloon. After application, the therapeutic formulation was dried in a forced air convection oven for about 60 minutes at about 50° C.

Example 4

A therapeutic formulation was made consisting of about 0.5 gm of zotarolimus and about 0.5 gm of polyethyleneimine (MW=10K) in about 9 gm of 200 proof ethanol. Using direct fluid application, about 53 μl of the therapeutic formulation was applied to a 6×40 mm FoxSV balloon resulting in a dose density of approximately 300 μg/cm$^2$.

Example 5

A solution was made of about 0.1 gm of poly(L-lysine) (hydrochloride salt, MW=30K) and about 0.01 gm TWEEN 20 in about 0.89 gm water. With mixing, this solution was added to 9 gm of 200 proof ethanol. After dissolving about 0.1 gm of zotarolimus, about 133 μl was applied to a 6×100 mm Fox SV balloon by direct fluid dispense to make a about 300 μg/cm$^2$ dose coating.

Example 6

A therapeutic formulation was made consisting of about 0.5 gm of sirolimus and about 0.5 gm of tranexamic acid in about 19 gm of 90/10 MeOH/Water (w/w). Using direct fluid application, about 110 μl of the therapeutic formulation was applied to a 6×40 mm FoxSV balloon resulting in a dose density of approximately 300 μg/cm$^2$.

The disclosed subject matter can be embodied in other specific forms without departing from its spirit or essential characteristics. The described embodiments are to be considered in all respects only as illustrative and not restrictive. Thus, it is intended that the disclosed subject matter include modifications and variations that are within the scope of the appended claims and their equivalents. All references recited herein are incorporated herein in their entirety by specific reference.

The invention claimed is:

1. A system for delivering a therapeutic agent to a vessel wall of a subject, comprising:
    a polymeric balloon having a distal end, a proximal end, and a working length therebetween; and
    a therapeutic formulation coating disposed on at least a portion of the working length of the balloon, the therapeutic formulation coating consisting essentially of a mixture of a therapeutic agent and a synthetic polycationic polymer, wherein the therapeutic agent is a cytostatic agent and the synthetic polycationic polymer promotes fibrin formation on the vessel wall to promote adhesion of the therapeutic formulation coating to the vessel wall, wherein the synthetic polycationic polymer is selected from the group consisting of polyethyleneimine, polyallylamine, poly(L-lysine), poly(D-lysine), poly(L-arginine), poly(D-arginine), poly(L-histidine), poly(D-histidine), and combinations thereof.

2. The system of claim 1, wherein the therapeutic agent is zotarolimus, and the synthetic polycationic polymer is polyethyleneimine.

3. The system of claim 2, wherein the ratio of zotarolimus:polyethyleneimine is about 1:1 by weight.

4. The system of claim 1, wherein the therapeutic agent is zotarolimus, and the synthetic polycationic polymer is poly(L-lysine).

5. The system of claim 4, wherein the ratio of zotarolimus:poly(L-lysine) is about 1:1 by weight.

6. The system of claim 1, wherein the therapeutic agent is selected from the group consisting of zotarolimus, sirolimus, rapamycin, everolimus, biolimus, myolimus, novolimus, temsirolimus, deforolimus, merilimus, sirolimus derivatives, tacrolimus, pimecrolimus, derivatives and analogues thereof, and combinations thereof.

7. The system of claim 1, wherein the cytostatic agent is crystalline.

8. The system of claim 1, further comprising a prosthesis mounted on the balloon.

9. The system of claim 8, wherein the prosthesis is a stent.

10. A method for manufacturing a system for delivering a therapeutic agent to a vessel wall of a subject, comprising:
    (a) providing a system comprising a polymeric balloon having a distal end, a proximal end, and a working length therebetween; and
    (b) disposing a therapeutic formulation coating on at least a portion of the working length of the balloon, wherein the therapeutic formulation coating consists essentially of a mixture of a therapeutic agent and a synthetic polycationic polymer;
    wherein the therapeutic agent is a cytostatic agent and the synthetic polycationic polymer promotes fibrin formation on the vessel wall to promote adhesion of the therapeutic formulation coating to the vessel wall, wherein the synthetic polycationic polymer is selected from the group consisting of polyethyleneimine, polyallylamine, poly(L-lysine), poly(D-lysine), poly(L-arginine), poly(D-arginine), poly(L-histidine), poly(D-histidine), and combinations thereof.

* * * * *